US008673956B2

(12) United States Patent
Bara

(10) Patent No.: US 8,673,956 B2
(45) Date of Patent: Mar. 18, 2014

(54) IMIDO-ACID SALTS AND METHODS OF USE

(71) Applicant: Board of Trustees of the University of Alabama, Tuscaloosa, AL (US)

(72) Inventor: Jason E. Bara, Northport, AL (US)

(73) Assignee: Board of Trustees of The University of Alabama, Tuscaloosa, AL (US)

( * ) Notice: Subject to any disclaimer, the term of this patent is extended or adjusted under 35 U.S.C. 154(b) by 0 days.

(21) Appl. No.: 13/688,346

(22) Filed: Nov. 29, 2012

(65) Prior Publication Data
US 2013/0143939 A1 Jun. 6, 2013

Related U.S. Application Data

(60) Provisional application No. 61/566,175, filed on Dec. 2, 2011.

(51) Int. Cl.
*C07D 233/64* (2006.01)
*C10L 3/10* (2006.01)
*B01D 53/14* (2006.01)
*A61K 31/4172* (2006.01)

(52) U.S. Cl.
USPC ............ 514/400; 548/341.1; 548/342.1; 48/127.3; 252/184; 210/750; 95/149

(58) Field of Classification Search
USPC .......................................... 548/341.1, 342.1
See application file for complete search history.

(56) References Cited

U.S. PATENT DOCUMENTS

| | | | |
|---|---|---|---|
| 4,088,735 A | 5/1978 | Bratzler et al. | |
| 4,624,838 A | 11/1986 | Pan et al. | |
| 4,775,519 A | 10/1988 | Yit Nieh | |
| 7,744,838 B2 | 6/2010 | Davis, Jr. | |
| 7,789,945 B2 | 9/2010 | Lechnick et al. | |
| 7,790,012 B2 | 9/2010 | Kirk et al. | |
| 2005/0010076 A1 | 1/2005 | Wasserscheid et al. | |
| 2005/0129598 A1 | 6/2005 | Chinn et al. | |
| 2007/0044658 A1 | 3/2007 | Rochelle et al. | |
| 2007/0093462 A1 | 4/2007 | Rogers et al. | |
| 2008/0029735 A1 | 2/2008 | Gin et al. | |
| 2008/0050296 A1 | 2/2008 | Tontiwachwuthikul et al. | |
| 2009/0171098 A1 | 7/2009 | Bara et al. | |
| 2009/0173693 A1 | 7/2009 | Gin et al. | |
| 2009/0291872 A1 | 11/2009 | Bara et al. | |
| 2009/0291874 A1 | 11/2009 | Bara et al. | |
| 2010/0086983 A1 | 4/2010 | Gellett et al. | |
| 2011/0014100 A1 | 1/2011 | Bara et al. | |
| 2011/0223087 A1 | 9/2011 | Lustig et al. | |
| 2011/0256043 A1 | 10/2011 | Blair et al. | |
| 2012/0294785 A1 | 11/2012 | Murai et al. | |

FOREIGN PATENT DOCUMENTS

WO    2009076530 A1    6/2009

OTHER PUBLICATIONS

Shannon et al., Reactive and Reversible Ionic Liquids for CO2 Capture and Acid Gas Removal, Separation Sci. and Technol., 47:178-188 (2012).

Shannon et al., Properties of alkylimidazoles as solvents for CO2 capture and comparisons to imidazolium-based ionic liquids, Ind. Eng. Chem. Res., 50(14):8665-8677 (2011).
Sharma et al., Mass Transfer and Solubility of CO and H2 in Ionic Liquid. Case of [Bmim][PF6] with Gas-Inducing Stirrer Reactor, Ind. Eng. Chem. Res., 48:4075-4082 (2009).
Smith et al., A comparison of fluoroalkyl derivatized imidazolium:TFSI and alkyl-derivatized imidazolium:TFSI ionic liquids: a molecular dynamics simulation study, Phys. Chem. Chem. Phys., 12(26):7064-7076 (2010).
Smith et al., A comparison of ether and alkyl derivatized imidazolium based room temperature ionic liquids: a molecular dynamics simulation study, Phys. Chemistry Chemical Phys., 10(4):6301-6312 (2008).
Strazisar et al., Degradation Pathways for Monoethanolamine in a CO2 Capture Facility, Energy Fuels, 17:1034-1039 (2003).
Tokuda et al., Physicochemical Properties and Structures of Room Temperature Ionic Liquids. 2. Variation of Alkyl Chain Length in Imidazolium Cation, J. Phys. Chem. B, 109:6103-6110 (2005).
Tokuda et al., How Ionic Are Room-Temperature Ionic Liquids? An Indicator of the Physicochemical Properties, J. Phys. Chem. B, 110:19593-19600 (2006).
Verevkin et al., Thermodynamics of Ionic Liquids Precursors: 1-Methylimidazole, J. Phys. Chem. B, 115 (15):4404-4411 (2011).
Wang et al., Carbon dioxide capture by superbase-derived ionic liquids, Angew. Chem. Int. Ed, 49(43):5978-5981 (2010).
Wasserscheid et al., 1-n-butyl-3-methylimidazolium ([bmim]) octylsulfate: An Even Greener Ionic Liquid, Green Chem., 4:400-404 (2002).
Widegren et al., Density, Viscosity, Speed of Sound, and Electrolytic Conductivity for the Ionic Liquid 1-Hexyl-3-methylimidazolium Bis(trifluoromethylsulfonyl)imide and Its Mixtures with Water, J. Chem. Eng. Data, 52:2331-2338 (2007).
Wolfenden et al., Monoalkyl sulfates as alkylating agents in water, alkylsulfatase rate enhancements, and the "energy-rich" nature of sulfate half-esters, Proc. Nat. Acad. Sci., 104:83-86 (2007).
Zhou et al., Densities and Viscosities of 1-Butyl-3-methylimidazolium Tetrafluoroborate + H2O Binary Mixtures from (303.15 to 353.15) K, J. Chem. Eng. Data, 51:905-908 (2006).
Office Action for U.S. Appl. No. 13/430,813 dated Feb. 8, 2013.
International Search Report and Written Opinion for Application No. PCT/US2012/030672 dated Sep. 12, 2012.
Ahosseini et al., Viscosity of Imidazolium-Based Ionic Liquids at Elevated Pressures: Cation and Anion Effects, Int. J. Thermophys., 29:1222-1243 (2008).
Anthony et al., Anion Effects on Gas Solubility in Ionic Liquids, J. Phys. Chem. B, 109:6366-6374 (2005).
Armand et al., Ionic-liquid materials for the electrochemical challenges of the future, Nat. Mater., 8:621-629 (2009).

(Continued)

*Primary Examiner* — Samantha Shterengarts
*Assistant Examiner* — Amanda L Aguirre
(74) *Attorney, Agent, or Firm* — Meunier Carlin & Curfman, LLC

(57) ABSTRACT

Imido-acid salts and compositions containing imido-acid salts are described herein. Methods of their preparation and use are also described herein. The methods of using the imido-acid salts include the reduction of volatile compounds from gas and liquid streams and the delivery of pharmaceutical agents to subjects.

24 Claims, No Drawings

(56) References Cited

OTHER PUBLICATIONS

Bara et al., Versatile and Scalable Method for Producing N-Functionalized Imidazoles, Ind. Eng. Chem. Res., 50 (24):13614-13619 (2011).
Bara et al., Room-Temperature Ionic Liquids and Composite Materials: Platform Technologies for CO2 Capture, Acc. Chem. Res., 43:152-159 (2010).
Bara et al., Guide to CO2 Separations in Imidazolium-based Room-Temperature Ionic Liquids, Ind. Eng. Chem. Res., 48(6):2739-2751 (2009).
Bara et al., Enhanced CO2 Separation Selectivity in Oligo(ethylene glycol) Functionalized Room-Temperature Ionic Liquids, Ind. Eng. Chem. Res., 46:5380-5386 (2007).
Bara et al., Gas Separations in Fluoroalkyl-functionalized Room-Temperature Ionic Liquids Using Supported Liquid Membranes, Chem. Eng. J., 147:43-50 (2009).
Bates et al., CO2 Capture by a Task-Specific Ionic Liquid, J. Am. Chem. Soc., 124:926-927 (2002).
Cadena et al., Why is CO2 so Soluble in Imidazolium-Based Ionic Liquids?, J. Am. Chem. Soc., 126:5300-5308 (2004).
Camper et al., Room-Temperature Ionic Liquid—Amine Solutions: Tunable Solvents for Efficient and Reversible Capture of CO2, Ind. Eng. Chem. Res., 47(21):8496-8498 (2008).
Carlisle et al., Interpretation of CO2 Solubility and Selectivity in Nitrile-functionalized Room-Temperature Ionic Liquids Using a Group Contribution Approach, Ind. Eng. Chem. Res., 47:7005-7012 (2008).
Carvalho et al., Effect of Water on the Viscosities and Densities of 1-Butyl-3-methylimidazolium Dicyanamide and 1-Butyl-3-methylimidazolium Tricyanomethane at Atmospheric Pressure, J. Chem. Eng. Data, 55:645-652 (2010).
Crosthwaite et al., Phase Transition and Decomposition Temperatures, Heat Capacities and Viscosities of Pyridinium Ionic Liquids, J. Chem. Thermodyn., 37:559-568 (2005).
Domanska et al., Temperature and Composition Dependence of the Density and Viscosity of Binary Mixtures of {1-Butyl-3-methylimidazolium Thiocyanate + 1-Alcohols}, J. Chem. Eng. Data, 54:2113-2119 (2009).
Emel'Yanenko et al., Building Blocks for ionic liquids: Vapor pressures and vaporization enthalpies of 1-(n-alkyl)-imidazoles, J. Chem. Thermodyn., 43(10):1500-1505 (2011).
Finotello et al., Room-temperature ionic liquids: Temperature dependence of gas solubility selectivity, Ind. Eng. Chem. Res., 47(10):3453-3459 (2008).
Finotello et al., Ideal gas solubilities and solubility selectivities in a binary mixture of room temperature ionic liquids, J. Phys. Chem. B, 112(8):2335-2339 (2008).
Fletcher et al., Physical Properties of Selected Ionic Liquids for Use as Electrolytes and Other Industrial Applications., J. Chem. Eng. Data, 55:778-782 (2010).
Gardas et al., A group contribution method for viscosity estimation of ionic liquids, Fluid Phase Equilibr., 266:195-201 (2008).
Ge et al., Densities and Viscosities of 1-Butyl-3-methylimidazolium Trifluoromethanesulfonate + H2O Binary Mixtures at T = (303.15 to 343.15) K, J. Chem. Eng. Data, 53:2408-2411 (2008).
Gomez et al., Physical Properties of Pure 1-Ethyl-3-methylimidazolium Ethylsulfate and Its Binary Mixtures with Ethanol and Water at Several Temperatures, J. Chem. Eng. Data, 51:2096-2102 (2006).
Gutowski et al., Amine-functionalized Task-Specific Ionic Liquids: A Mechanistic Explanation for the Dramatic Increase in Viscosity upon Complexation with CO2 from Molecular Simulation, J. Am. Chem. Soc., 130:14690-14704 (2008).
Han et al., Ionic Liquids in Separations, Acc. Chem. Res., 40:1079-1086 (2007).
Harper et. al., Survey of Carbon Dioxide Capture in Phosphonium-Based Ionic Liquids and End-Capped Polyethylene Glycol Using DETA (DETA = Diethylenetriamine) as a Model Absorbent, Ind. Eng. Chem. Res., 50:2822-2830 (2011).
Harris et al., Temperature and Pressure Dependence of the Viscosity of the Ionic Liquid 1-Butyl-3-methylimidazolium Tetrafluoroborate: Viscosity and Density Relationships in Ionic Liquids, J. Chem. Eng. Data, 52: 2425-2430 (2007).
Hasib-Ur-Rahman et al., CO2 capture in alkanolamine/room-temperature ionic liquid emulsions: A viable approach with carbamate crystallization and curbed corrosion behavior, Int. J. Greenh. Gas Control, 6:246-252 (2012).
Huang et. al., Chloride ion enhanced thermal stability of carbon dioxide captured by monoethanolamine in hydroxyl imidazolium based ionic liquids, Energy Environ. Sci., 4:2125-2133 (2011).
Jacquemin et al., Thermophysical Properties, Low Pressure Solubilities and Thermodynamics of Solvation of Carbon Dioxide and Hydrogen in Two Ionic Liquids Based on the Alkylsulfate Anion, Green Chem., 10:944-950 (2008).
Jacquemin et al., Density and Viscosity of Several Pure and Watersaturated Ionic Liquids. Green Chem., 8:172-180 (2006).
Karadas et al., Review on the Use of Ionic Liquids (ILs) as Alternative Fluids for CO2 Capture and Natural Gas Sweetening, Energ. Fuels, 24:5817-5828 (2010).
Kim et al., Significantly Enhanced Reactivities of the Nucleophilic Substitution Reactions in Ionic Liquid, J. Org. Chem., 68:4281-4285 (2003).
LaFrate et al., Accelerated Aging and Degradation Analysis of CO2 Capture Solvents Containing Ionic Liquids, DOE degradation paper, Energy & Fuels, p. 1-12 (Apr. 30, 2012).
LaFrate et al., High Water Vapor Flux Membranes Based on Novel Diol-Imidazolium Polymers, Ind. Eng. Chem. Res., 49:11914-11919 (2010).
Lepaumier et al., Degradation of MMEA at absorber and stripper conditions, Chem. Eng. Sci., 66:3491-3498 (2011).
Lin et al., Materials selection guidelines for membranes that remove CO2 from gas mixtures, J. Mol. Struct., 739:57-74 (2005).
Mokhtarani et al., Density and Viscosity of 1-butyl-3-methylimidazolium Nitrate with Ethanol, 1-propanol, or 1-butanol at Several Temperatures, J. Chem. Thermodyn., 41:1432-1438 (2009).
Mokhtarani et al., Densities, Refractive Indices, and Viscosities of the Ionic Liquids 1-Methyl-3-octylimidazolium Tetrafluoroborate and 1-Methyl-3-butylimidazolium Perchlorate and Their Binary Mixtures with Ethanol at Several Temperatures, J. Chem. Eng. Data, 53:677-682 (2008).
Muhammad et al., Thermophysical Properties of 1-hexyl-3-methyl Imidazolium Based Ionic Liquids with Tetrafluoroborate, Hexafluorophosphate and bis(trifluoromethylsulfonyl)imide Anions, J. Chem. Thermodyn., 40:1433-1438 (2008).
NETL, Carbon Sequestration Technology Roadmap and Program Plan (2007).
NETL, Existing Plants, Emissions and Capture—Setting CO2 Program Goals, DOE/NETL-2009/1366.
Pereiro et al., Physical Properties of 1-Butyl-3-methylimidazolium Methyl Sulfate as a Function of Temperature, Chem. Eng. Data, 52:377-380 (2007).
Pereiro et al., Physical Properties of Ionic Liquids Based on 1-alkyl-3-methylimidazolium Cation and Hexafluorophosphate as Anion and Temperature Dependence, J. Chem. Thermodyn., 39:1168-1175 (2007).
Rochelle, Amine Scrubbing for CO2 Capture, Science, 325:1652-1654 (2009).
Rodriguez et al., Temperature and Composition Dependence of the Density and Viscosity of Binary Mixtures of Water + Ionic Liquid, J. Chem. Eng. Data, 51:2145-2155 (2006).
Sanchez et al., Density, Viscosity, and Surface Tension of Synthesis Grade Imidazolium, Pyridinium, and Pyrrolidinium Based Room Temperature Ionic Liquids, Chem. Eng. Data, 54:2803-2812 (2009).
Sanmamed et al., Viscosity-induced errors in the density determination of room temperature ionic liquids using vibrating tube densitometry, Fluid Phase Equilibr., 252:96-102 (2007).
Schreiner et al., Fractional Walden Rule for Ionic Liquids: Examples from Recent Measurements and a Critique of the So-Called Ideal KCI Line for the Walden Plot, J. Chem. Eng. Data, 55:1784-1788 (2010).
Seddon et al., Viscosity and Density of 1-Alkyl-3-methylimidazolium Ionic Liquids, ACS Symp. Ser., 819:34-49 (2002).

(56) References Cited

OTHER PUBLICATIONS

Shannon et al., Evaulation of Alkylimidazoles as Physical Solvents for CO2/CH4 Separation, Ind. Eng. Chem Res., 51:515-522 (2012).
Hu et al., Novel Ag(1) complexes with azole heterocycle ligands bearing acetic acid group: synthesis, characterization and crystal structures, Cryst. Eng. Comm., 10:1037-1043 (2008).
International Search Report and Written Opinion for Application No. PCT/US2012/066967 dated Mar. 19, 2013.
Wang et al., Tuning the Basicity of Ionic Liquids for Equimolar C02 capture, Angewandte Chemie International Ed., 50:4918-4922 (2011).

IMIDO-ACID SALTS AND METHODS OF USE

CROSS-REFERENCE TO PRIORITY APPLICATION

This application claims the benefit of priority to U.S. Provisional Application No. 61/566,175, filed Dec. 2, 2011, which is incorporated herein by reference in its entirety.

FIELD

The subject matter disclosed herein generally relates to imido-acid salts and methods of their preparation. Also, the subject matter described herein generally relates to methods of using the imido-acid salts to capture and reduce volatile compounds from gas and liquid streams. Further, the subject matter described herein generally relates to methods of using the imido-acid salts to deliver pharmaceutical agents to subjects.

BACKGROUND

There is a worldwide interest in capturing and sequestering or reusing carbon dioxide ($CO_2$) emissions to stabilize the climate. Aqueous amine processes, widely used throughout the natural gas industry to reduce $CO_2$ from gas streams via chemical reaction, represent the benchmark by which $CO_2$ capture technologies are evaluated (NETL, Carbon Sequestration Technology Roadmap and Program Plan (2007); Rochelle, G. T., "Amine Scrubbing for $CO_2$ Capture," Science, 325:1652-1654 (2009)). While effective at reducing $CO_2$ from gas streams, amine processes are highly energy intensive, with much of the energy penalty attributed to boiling water during amine regeneration. Thus, aqueous amine processes will inherently suffer from large energy penalties. However, new solvents with little or no volatility can provide the desired energy efficiency.

Amino acid salts have been proposed as a type of "advanced" amine for $CO_2$ capture. Amino acid salts are neutralized forms (i.e., metal salts) of naturally occurring amido acids such as glycine. Aqueous solutions of amino acid salts, such as sodium glycinate, represent alternatives to conventional amine-based solvents for post-combustion $CO_2$ capture applications.

Relative to amines, amino acid salts can feature benefits of reduced amine volatility (due to the ionic nature of the compound), greater stability in the presence of oxidizers found in flue gas (e.g., $O_2$, $SO_2$, and $NO_R$), and a more rapid reaction rate with $CO_2$, likely due to the enhanced basicity of solvent due to the presence of a basic carboxylate paired with an amine. Amino acid salts are thus a promising approach. However, because the salts are based on a narrow range of naturally occurring compounds, amino acid salts are limited in the tunability of their structures to drive improved $CO_2$ capture applications. Thus, alternative structures with increased tunability are needed.

SUMMARY

In accordance with the purposes of the disclosed materials, compounds, compositions, and methods, as embodied and broadly described herein, the disclosed subject matter, in one aspect, relates to systems and compositions including imido-acid salts and methods for preparing and using such systems and compositions. In a further aspect, the disclosed subject matter relates to methods of using the imido-acid salts described herein to capture and reduce volatile compounds from gas and liquid streams. In a still further aspect, the disclosed subject matter described herein generally relates to methods of using the imido-acid salts to deliver pharmaceutical agents to subjects. Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

The materials, compounds, compositions, articles, and methods described herein may be understood more readily by reference to the following detailed description of specific aspects of the disclosed subject matter and the examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., volatile compounds in a stream). It is understood that this is typically in relation to some standard or expected value, in other words it is relative, but that it is not always necessary for the standard or relative value to be referred to. For example, "reduces $CO_2$" means reducing the amount of $CO_2$ in a stream relative to a standard or a control. As used herein, reduce can include complete removal. In the disclosed method, reduction can refer to a 10%, 20%, 30%, 40%, 50%, 60%, 70%, 80%, 90%, or 100% decrease as compared to the standard or a control. It is understood that the terms "sequester," "capture," "remove," and "separation" are used synonymously with the term "reduce."

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to add or mix two or more compounds, compositions, or materials under appropriate conditions to produce a desired product or effect (e.g., to reduce or eliminate a particular characteristic or event such as $CO_2$ reduction). The terms "contact" and "react" are used synonymously with the term "treat."

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

The term "ion," as used herein, refers to any molecule, portion of a molecule, cluster of molecules, molecular complex, moiety, or atom that contains a charge (positive, negative, or both at the same time within one molecule, cluster of molecules, molecular complex, or moiety (e.g., Zwitterion)).

The term "anion" is a type of ion and is included within the meaning of the term "ion." An "anion" is any molecule, portion of a molecule (e.g., Zwitterion), cluster of molecules, molecular complex, moiety, or atom that contains a net negative charge.

The term "cation" is a type of ion and is included within the meaning of the term "ion." A "cation" is any molecule, portion of a molecule (e.g., Zwitterion), cluster of molecules, molecular complex, moiety, or atom, that contains a net positive charge.

The term "non-ionic" as used herein refers to being free of ionic groups or groups that are readily substantially ionized in water. A "non-ionic" compound does not contain a charge at neutral pH (e.g., at a pH from 6.7 to 7.3). However, non-ionic compounds can be made to have a charge under acidic or basic conditions or by methods known in the art, e.g., protonation, deprotonation, oxidation, reduction, alkylation, acetylation, esterification, deesterification, hydrolysis, etc. Thus, the disclosed "non-ionic" compounds can become ionic under conditions where an acidic proton is available to protonate the compound.

The term "volatile compound" as used herein refers to chemical compounds that are capable of vaporizing. The "volatile compounds" described herein are found in the streams and have higher vapor pressures than the stream, such as natural gas feeds. Volatile compounds include light gases and acid gases, such as $CO_2$, $O_2$, $N_2$, $CH_4$, $H_2$, hydrocarbons, $H_2S$, $SO_2$, NO, $NO_2$, COS, $CS_2$, and the like.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below. "Heteroalkyl" is defined as an alkyl group that has at least one heteroatom incorporated within the alkyl chain. Examples of heteroatoms include, but are not limited to, nitrogen, oxygen, sulfur, and phosphorus.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C{=}C(A^3A^4)$ are intended to include both the E and Z isomers. This can be presumed in structural formulae herein wherein an asymmetric alkene is present, or it can be explicitly indicated by the bond symbol C═C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below. "Heteroalkenyl" is defined as an alkenyl group that has at least one heteroatom incorporated within the alkenyl chain. Examples of heteroatoms include, but are not limited to, nitrogen, oxygen, sulfur, and phosphorus.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below. "Heteroalkynyl" is defined as an alkynyl group that has at least one heteroatom incorporated within the alkynyl chain. Examples of heteroatoms include, but are not limited to, nitrogen, oxygen, sulfur, and phosphorus.

The term "aryl" as used herein is a group that contains any carbon-based aromatic group including, but not limited to, benzene, naphthalene, phenyl, biphenyl, phenoxybenzene, and the like. "Heteroaryl" is defined as an aromatic group that has at least one heteroatom incorporated within the ring of the aromatic group. Examples of heteroatoms include, but are not limited to, nitrogen, oxygen, sulfur, and phosphorus. The term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one carbon-carbon double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkynyl" as used herein is a non-aromatic carbon-based ring composed of at least three carbon atoms and containing at least one carbon-carbon triple bound. Examples of cycloalkynyl groups include, but are not limited to, cyclobutynyl, cyclopentynyl, cyclohexynyl, cyclooctynyl, and the like. The term "heterocycloalkynyl" is a type of cycloalkynyl group as defined above where at least one of the carbon atoms of the ring is substituted with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a short hand notation for C=O.

The term "amino" as used herein is represented by the formula —$NA^1A^2$, where $A^1$ and $A^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" or "carboxyl" group as used herein is represented by the formula —C(O)O$^-$.

The term "ester" as used herein is represented by the formula —OC(O)$A^1$ or —C(O)O$A^1$, where $A^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "nitro" as used herein is represented by the formula —$NO_2$.

The term "silyl" as used herein is represented by the formula —Si$A^1A^2A^3$, where $A^1$, $A^2$, and $A^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —S(O)$_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

The term "thiol" as used herein is represented by the formula —SH.

The term "thio" as used herein is represented by the formula —S—.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods.

Materials and Compositions

Disclosed herein are materials, compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a composition is disclosed and a number of modifications that can be made to a number of components of the composition are discussed, each and every combination and permutation that are possible are specifically contemplated unless specifically indicated to the contrary. Thus, if a class of components A, B, and C are disclosed as well as a class of components D, E, and F and an example of a combination composition A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

Imido-Acid Salts

Imido-acid salts are a class of organic compounds represented by Formula I:

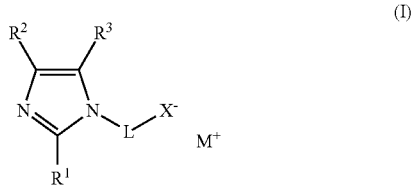

(I)

and derivatives thereof.

In Formula I, L is selected from substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, or substituted or unsubstituted $C_{2-20}$ heteroalkynyl. In some embodiments, L is a substituted or unsubstituted $C_{1-12}$ alkyl, such as a $C_{1-10}$ alkyl or a $C_{1-6}$ alkyl. For example, L can be a propyl group.

Also in Formula I, $M^+$ is selected from hydron, a metal cation, a therapeutic agent cation, a substituted or unsubstituted heterocycloalkyl cation, a substituted or unsubstituted heteroaryl cation, a substituted or unsubstituted ammonium, or a substituted or unsubstituted phosphonium. The metal cation can be a Group I metal, a Group II metal, a transition metal, or a lanthanide metal. Examples of suitable metal cations include, for example, cations of iron ($Fe^{2+}$ and $Fe^{3+}$), magnesium ($Mg^{2+}$), manganese ($Mn^{2+}$), chromium ($Cr^{2+}$ and $Cr^{3+}$), sodium ($Na^+$), potassium ($K^+$), lithium ($Li^+$), zinc ($Zn^+$), calcium ($Ca^{2+}$), and aluminum ($Al^{3+}$).

In some embodiments, M can be a therapeutic agent and, likewise, $M^+$ can be the positively charged therapeutic agent (i.e., a therapeutic agent cation). In these examples, the therapeutic agent is an existing drug that is cationic or that can be made cationic. Many drugs exist naturally or at physiological conditions as cations, or they can be converted to cations via simple chemical transformations (e.g., alkylation, protonation, deprotonation, etc.).

In other embodiments, $M^+$ can be a substituted or unsubstituted heterocycloalkyl cation. Examples of suitable heterocycloalkyl cations include substituted or unsubstituted piperidinium and pyrrolidinium. In still other embodiments, $M^+$ can be a substituted or unsubstituted heteroaryl cation. Examples of suitable heteroaryl cations include substituted or unsubstituted pyridinium, pyridazinium, pyrimidinium, pyrazinium, imidazolium, pyrazolium, oxazolium, triazolium (e.g., 1,2,3-triazolium and 1,2,4-triazolium), thiazolium, quinolium, isoquinolium, and the like, including substituted derivatives and mixtures thereof.

Additionally in Formula I, $R^1$, $R^2$, and $R^3$ are each independently selected from hydrogen, halogen, hydroxyl, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, substituted or unsubstituted silyl, substituted or unsubstituted alkoxyl, substituted or unsubstituted aryloxyl, substituted or unsubstituted amino, cyano, thio, or nitro.

In some embodiments, adjacent R groups (i.e., $R^2$ and $R^3$) can be combined to form a substituted or unsubstituted aryl, substituted or unsubstituted heteroaryl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, or substituted or unsubstituted heterocycloalkynyl.

Further in Formula I, $X^-$ is selected from a carboxylate, a sulfonate, or a phosphate. In some embodiments, $X^-$ can be $CO_2^-$ or $SO_3-$.

In some embodiments, the imido-acid salt represented by Formula I can be an imido carboxylate salt, as represented by Formula I-A. In other embodiments, the imido-acid salt represented by Formula I can be an imido sulfonate salt, as represented by Formula I-B.

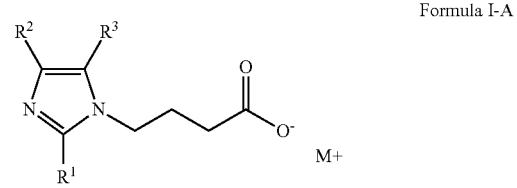

Formula I-A

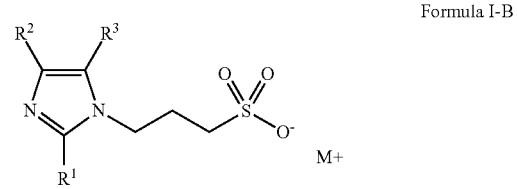

Formula I-B

In certain examples, the imido-acid salt is not 1H-imidazole-1-butanoic acid, 1H-imidazole-1-pentanoic acid, or 1H-Imidazole-1-butanesulfonic acid.

Imido-Acid Salt Systems for Treating Gas and Liquid Streams

The imido-acid salts described herein can be included in systems used to capture and reduce volatile compounds, such as carbon dioxide ($CO_2$), carbon monoxide (CO), sulfur dioxide ($SO_2$), hydrogen sulfide ($H_2S$), nitrogen oxide (NO), nitrogen dioxide ($NO_2$), carbonyl sulfide (COS), and carbon disulfide ($CS_2$), mercaptans, $H_2O$, $O_2$, $H_2$, $N_2$, $C_1$-$C_8$ hydrocarbons (e.g., methane and propane), volatile organic compounds, and mixtures of these and other volatile compounds from gas streams and liquid streams. Additional components that can optionally be included in the systems include amines, imidazoles, and ionic liquids.

Amines

In some embodiments, the systems including imido-acid salts can further comprise one or more amine compounds. The amine can be a primary amine, a secondary amine, a tertiary amine, a cyclic amine, or a mixture thereof. The amine compounds described herein can be represented by Formula II:

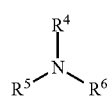

(II)

In Formula II, $R^4$, $R^5$, and $R^6$ can each independently be selected from the group consisting of hydrogen, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, substituted or unsubstituted thio, substituted or unsubstituted amino, substituted or unsubstituted alkoxyl, substituted or unsubstituted aryloxyl, silyl, siloxyl, or cyano.

In some embodiments, the amine can be a primary amine. According to these examples, two of $R^4$, $R^5$, or $R^6$ are hydrogen and the remaining group is other than hydrogen to form, for example, a compound according to Formula II-A.

Formula II-A

In Formula II-A, $R^4$ is selected from substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, substituted or unsubstituted thio, substituted or unsubstituted amino, substituted or unsubstituted alkoxyl, or substituted or unsubstituted aryloxyl. Particular examples of primary amines as described herein include monoethanolamine (MEA), diglycolamine (DGA), and 2-amino-2-methylpropanol (AMP).

In some embodiments, the amine can be a secondary amine where one of $R^4$, $R^5$, or $R^6$ is hydrogen and the remaining two groups are other than hydrogen. Secondary amines as described herein can be represented, for example, by Formula II-B.

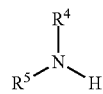

Formula II-B

In Formula II-B, $R^4$ and $R^5$ are each independently selected from substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, substituted or unsubstituted thio, substituted or unsubstituted amino, substituted or unsubstituted alkoxyl, or substituted or unsubstituted aryloxyl. Particular examples of secondary amines as described herein include diethanolamine (DEA) and diisopropanolamine (DIPA).

In further embodiments, the amine can be a tertiary amine where each of $R^4$, $R^5$, and $R^6$ are other than hydrogen as represented by Formula II-C.

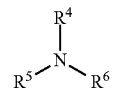

Formula II-C

In Formula II-C, $R^4$, $R^5$, and $R^6$ are each independently selected from substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, substituted or unsubstituted thio, substituted or unsubstituted amino, substituted or unsubstituted alkoxyl, or substituted or unsubstituted aryloxyl. A particular example of a tertiary amine includes N-methyldiethanolamine (MDEA).

The amines for use in the systems described herein can also include cyclic amines. According to these examples, two of $R^4$, $R^5$, or $R^6$ can combine to form a substituted or unsubstituted aryl, substituted or unsubstituted heteroaryl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, or substituted or unsubstituted heterocycloalkynyl. The cyclic amines can be represented by Formula II-D.

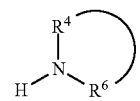

Formula II-D

In Formula II-D, the line connecting $R^4$ and $R^6$ represents a connection between $R^4$ and $R^6$ that forms a cyclic structure including $R^4$, N, and $R^6$. An example of a suitable cyclic amine for use in the systems described herein includes a substituted or unsubstituted piperazine (PZ).

The amine described herein can contain one amino functional group (i.e., can be a monoamine) or can contain two amino functional groups (i.e., can be a diamine), or can contain more than two amino functional groups (i.e., can be a polyamine).

Imidazoles

The systems described herein can optionally include one or more substituted or unsubstituted imidazoles. In some examples, the imidazoles for use in the systems described herein include N-functionalized imidazoles as represented by Formula III:

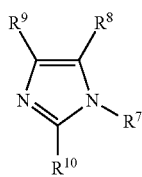

and derivatives thereof.

In Formula III, $R^7$ is substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, substituted or unsubstituted thio, substituted or unsubstituted amino, substituted or unsubstituted alkoxyl, substituted or unsubstituted aryloxyl, silyl, siloxyl, or cyano.

Also in Formula III, $R^8$, $R^9$, and $R^{10}$ are each independently selected from hydrogen, halogen, hydroxyl, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, substituted or unsubstituted thio, substituted or unsubstituted alkoxyl, substituted or unsubstituted aryloxyl, substituted or unsubstituted amino, cyano, or nitro.

Further in Formula III, adjacent R groups, i.e., $R^7$ and $R^8$, $R^7$ and $R^{10}$, and $R^8$ and $R^9$, can be combined to form a substituted or unsubstituted aryl, substituted or unsubstituted heteroaryl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, or substituted or unsubstituted heterocycloalkynyl. $R^7$, $R^8$, $R^9$, and $R^{10}$ can each also be halides, cyano, nitro, and other similar groups.

Examples of suitable N-functionalized imidazoles for use in the systems described herein include N-alkyl imidazoles, N-alkenyl imidazoles, N-aryl imidazoles, and mixtures of these.

Ionic Liquids

Optionally, the systems described herein can further include one or more ionic liquids. The ionic liquids that can be used in the disclosed methods and compositions comprise ionized species (i.e., cations and anions) and have melting points below about 150° C. For example, the disclosed ionic liquids can be liquid at or below a temperature of about 120° C. or about 100° C., and at or above a temperature of about −100° C. or about −44° C.

Ionic liquids contain one or more types of cations and one or more types of anions. In the systems described herein, the ionic liquids can include a substituted or unsubstituted imidazolium cation and an anion, wherein the anion includes a compound as represented by Formula IV:

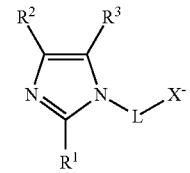

In Formula IV, L is selected from substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, or substituted or unsubstituted $C_{2-20}$ heteroalkynyl. In some embodiments, L is a substituted or unsubstituted $C_{1-12}$ alkyl, such as a $C_{1-10}$ alkyl or a $C_{1-6}$ alkyl. For example, L can be a propyl group.

Additionally in Formula IV, $R^1$, $R^2$, and $R^3$ are each independently selected from hydrogen, halogen, hydroxyl, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, substituted or unsubstituted silyl, substituted or unsubstituted thio, substituted or unsubstituted alkoxyl, substituted or unsubstituted aryloxyl, substituted or unsubstituted amino, cyano, or nitro.

In some embodiments, adjacent R groups (i.e., $R^2$ and $R^3$) can be combined to form a substituted or unsubstituted aryl, substituted or unsubstituted heteroaryl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, or substituted or unsubstituted heterocycloalkynyl.

Further in Formula IV, $X^-$ is selected from a carboxylate, a sulfonate, or a phosphate. In some embodiments, $X^-$ can be $CO_2^-$ or $SO_3^-$.

In some embodiments, the ionic liquids as can be represented by Formula IV-A:

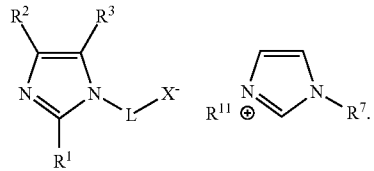

In these examples, $R^1$, $R^2$, $R^3$, $R^7$, L, and $X^-$ are as defined above and $R^{11}$ can be substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, substituted or unsubstituted thio, substituted or unsubstituted amino, substituted or unsubstituted alkoxyl, substituted or unsubstituted aryloxyl, silyl, siloxyl, or cyano.

Further ionic liquids can be included in the systems described herein. As noted, ionic liquids contain one or more types of cations and one or more types of anions. Suitable cations used to form ionic liquids can include substituted or unsubstituted pyridiniums, pyridaziniums, pyrimidiniums, pyraziniums, imidazoliums, pyrazoliums, oxazoliums, 1,2,3-triazoliums, 1,2,4-triazoliums, thiazoliums, piperidiniums, pyrrolidiniums, quinoliums, isoquinoliums, ammoniums, alkoxyalkyl imidazoliums, alkanolyl substituted ammoniums, alkoxyalkyl substituted ammoniums, aminoalkyl substituted ammoniums, arylalkyl substituted ammoniums, and the like. Suitable anions used to form the ionic liquids for use in the systems described herein can include halides (i.e., fluoride, chloride, bromide, or iodide), perchlorate, carboxylates, sulfates, sulfites, phosphates, phosphonates, phosphites, nitrate, nitrites, hypochlorite, chlorite, bicarbonates, and the like.

Systems

As described above, the systems disclosed herein can contain one or more imido-acid salts and optionally, one or more amines, imidazoles, or ionic liquids. The systems disclosed herein can be neat (i.e., can be composed of the imido-acid salts, amines, imidazoles, and/or ionic liquids without any additional solvent) or can be dissolved or dispersed in one or more additional solvents. In some embodiments, the system is an aqueous system comprised primarily of one or more imido-acid salts and water.

In some embodiments, the system is an aqueous system composed of a mixture of one or more imido-acid salts as described herein and one or more amines as described herein (i.e., an imido-acid salt/amine blend). The imido-acid salts can comprise 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% of the system, where any of the stated values can form an upper or lower endpoint of a range. In further examples, the imido-acid salts can comprise from 1% to 99%, 10% to 90%, 20% to 80%, 30% to 70%, 40% to 60%, or 50% of the system.

Likewise, the amine can comprise 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% of the system, where any of the stated values can form an upper or lower endpoint of a range. In further examples, the amine can comprise from 1% to 99%, 10% to 90%, 20% to 80%, 30% to 70%, 40% to 60%, or 50% of the system.

In some embodiments, the imido-acid salt/amine blend can further include one or more imidazoles as described herein and/or one or more ionic liquids as described herein. The imidazoles and ionic liquids can be included in the system in an amount of 20% by weight or less of the system. For example, the combined weight of the imidazole and ionic liquid in the system can be 20%, 19%, 18%, 17%, 16%, 15%, 14%, 13%, 12%, 11%, 10%, 9%, 8%, 7%, 6%, 5%, 4%, 3%, 2%, or 1% of the system, where any of the stated values can form an upper or lower endpoint of a range.

Imido-Acid Salts and Pharmaceutical Compositions

The imido-acid salts described herein can be used to deliver therapeutic or pharmaceutical agents to subjects when the imido-acid salt according to Formula I includes a therapeutic agent as M. Examples of therapeutic agents suitable for use in the imido-acid salts include adrenocortical steroids; adrenocortical suppressants; aldosterone antagonists; amino acids; anabolics; androgens; antagonists; anthelmintics; anti-acne agents; anti-adrenergics; anti-allergics; anti-amebics; anti-androgens; anti-anemics; anti-anginals; anti-arthritics; anti-asthmatics; anti-atherosclerotics; antibacterials; anticholelithics; anticholelithogenics; anticholinergics; anticoagulants; anticoccidals; antidiabetics; antidiarrheals; antidiuretics; antidotes; anti-estrogens; antifibrinolytics; antifungals; antiglaucoma agents; antihemophilics; antihemorrhagics; antihistamines; antihyperlipidemias; antihyperlipoproteinemics; antihypertensives; antihypotensives; anti-infective agents; anti-inflammatory agents; antikeratinizing agents; antimalarial; antimicrobials; antimitotics; antimycotics, antineoplastics, antineutropenics, antiparasitics; antiperistaltics, antpneumocystics; antiproliferatives; antiprostatic hypertrophy agents; antiprotozoals; antipruritics; antipsoriatics; antirheumatics; antischistosomals; antiseborrheics; antisecretory agents; antispasmodics; antithrombotics; antitussives; anti-ulcerative agents; anti-urolithics; antivirals; appetite suppressants; benign prostatic hyperplasia therapy agents; bone resorption inhibitors; bronchodilators; carbonic anhydrase inhibitors; cardiac depressants; cardioprotectants; cardiotonics; cardiovascular agents; choleretics; cholinergics; cholinergic agonists; cholinesterase deactivators; coccidiostat agents; diagnostic aids; diuretics; ectoparasiticides; enzyme inhibitors; estrogens; fibrinolytics; free oxygen radical scavengers; glucocorticoids; gonad-stimulating principle agents; hair growth stimulants; hemostatics; hormones; hypocholesterolemics; hypoglycemics; hypolipidemics; hypotensives; immunizing agents; immunomodulators; immunoregulators; immuno stimulants; immunosuppressants; impotence therapy adjuncts; inhibitors; keratolytics; LHRH agonists; liver disorder treatments, luteolysins; mucolytics; mydriatics; nasal decongestants; neuromuscular blocking agents; non-hormonal sterol derivatives; oxytocics; plasminogen activators; platelet activating factor antagonists; platelet aggregation inhibitors; potentiators; progestins; prostaglandins; prostate growth inhibitors; prothyrotropins; pulmonary surface agents; radioactive agents; regulators; relaxants; repartitioning agents; scabicides; sclerosing agents; selective adenosine A1 antagonists; steroids; suppressants; symptomatic multiple sclerosis agents; synergists; thyroid hormones; thyroid inhibitors; thyromimetics; amyotrophic lateral sclerosis agents; Paget's disease agents; unstable angina agents; uricosurics; vasoconstrictors; vasodilators; vulnerary agents; wound healing agents; and xanthine oxidase inhibitors.

In some examples, the imido-acid salts containing therapeutic agents described herein or derivatives thereof can be provided in a pharmaceutical composition. The compositions can include one or more of the compounds described herein and a pharmaceutically acceptable carrier. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI, Inc.; Bridgewater, N.J.), polyethylene glycol (PEG), and PLURONICS™ (BASF; Florham Park, N.J.).

Depending on the intended mode of administration, the pharmaceutical composition can be in the form of solid, semisolid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, can include other medicinal agents, pharmaceutical agents, carriers, or diluents.

Compositions containing the compound described herein or derivatives thereof suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like can also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms can also comprise buffering agents.

Solid compositions of a similar type can also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They can contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compositions described herein or derivatives thereof include pharmaceutically acceptable emulsions, solutions, suspensions, syrups, and elixirs. In addition to the active compounds, the liquid dosage forms can contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, can contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or derivatives thereof for rectal administrations are optionally suppositories, which can be prepared by mixing the compounds with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Preparation of the Imido-Acid Salts

The imido-acid salts according to Formula I and the additional, optional components of the system according to Formula II, Formula III, and Formula IV can be prepared in a variety of ways known to one skilled in the art of organic synthesis or variations thereon as appreciated by those skilled in the art. The compounds described herein can be prepared from readily available starting materials. Optimum reaction conditions can vary with the particular reactants or solvents used, but such conditions can be determined by one skilled in the art. The use of protection and deprotection, and the selection of appropriate protecting groups can be determined by one skilled in the art. The chemistry of protecting groups can be found, for example, in Wuts and Greene, *Protective Groups in Organic Synthesis*, 4th Ed., Wiley & Sons, 2006, which is incorporated herein by reference in its entirety.

Variations on Formula I, Formula II, Formula III, and Formula IV include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups.

The imido-acid salts and other components or the starting materials and reagents used in preparing the disclosed compounds are either available from commercial suppliers such as Aldrich Chemical Co., (Milwaukee, Wis.), Acros Organics (Morris Plains, N.J.), Fisher Scientific (Pittsburgh, Pa.), Sigma (St. Louis, Mo.), Pfizer (New York, N.Y.), GlaxoSmithKline (Raleigh, N.C.), Merck (Whitehouse Station, N.J.), Johnson & Johnson (New Brunswick, N.J.), Aventis (Bridgewater, N.J.), AstraZeneca (Wilmington, Del.), Novartis (Basel, Switzerland), Wyeth (Madison, N.J.), Bristol-Myers-Squibb (New York, N.Y.), Roche (Basel, Switzerland), Lilly (Indianapolis, Ind.), Abbott (Abbott Park, Ill.), Schering Plough (Kenilworth, N.J.), or Boehringer Ingelheim (Ingelheim, Germany), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

As shown in Scheme 1, the imido-acid salts described by Formula I-A can be made, for example, by reacting an imidazolate salt (1) with a lactone (2) to form the imido carboxylate salt (3).

Scheme 1:

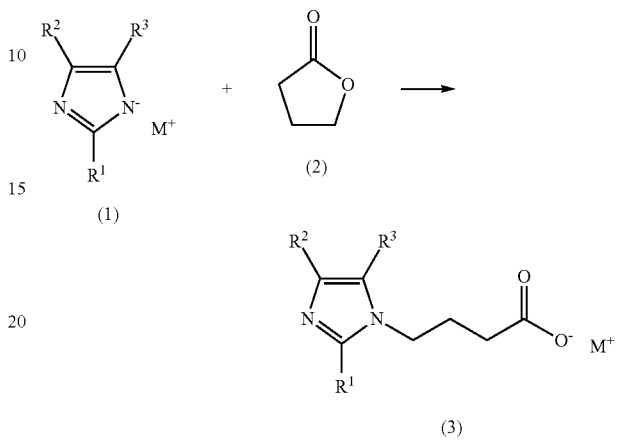

In addition, the imido-acid salts described by Formula I-B can be made, for example, by reacting an imidazolate salt (1) with a sultone (4) to form the imido sulfonate salt (5) (see Scheme 2).

Scheme 2:

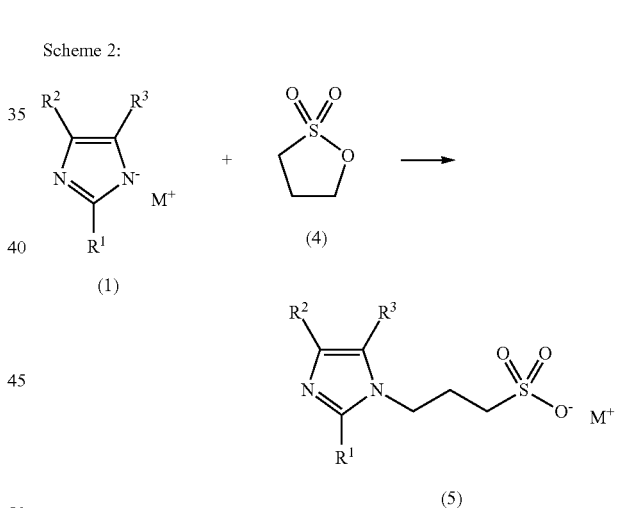

The disclosed systems including the imido-acid salts can be prepared by methods described herein. Generally, the particular imido-acid salts and optional components, including the amines, imidazoles, and ionic liquids, used to prepare the systems are selected as described herein. Then, with the particular imido-acid salts and optional components in hand, they can be combined, resulting in a system as described herein.

Methods of Using the Systems

The systems described herein can be used to reduce volatile compounds from streams (e.g., gas streams or liquid streams) as described in U.S. Published Patent Application Number 2009/0291874, which is incorporated by reference herein for its methods and techniques of volatile compound reduction. As used herein, volatile compounds can include to undesirable gaseous components found in a source and having a molecular weight lower than 150 g/mol. For example, the volatile compounds can have a molecular weight lower than 140 g/mol, 130 g/mol, 120 g/mol, 110 g/mol, 100 g/mol, 90 g/mol, 80 g/mol, 70 g/mol, 60 g/mol, 50 g/mol, 40 g/mol, 30 g/mol, 20 g/mol, or the like, where any of the stated values can form an upper or lower endpoint of a range. Examples of volatile compounds include $CO_2$, CO, COS, $H_2S$, $SO_2$, NO, $N_2O$, mercaptans, $H_2O$, $O_2$, $H_2$, $N_2$, $C_1$-$C_8$ hydrocarbons (e.g., methane and propane), volatile organic compounds, and mixtures of these.

The method for reducing a volatile compound from a stream can include contacting the stream with an effective amount of a composition as described herein. In some embodiments, the system is comprised primarily of an imido-acid salt. In other embodiments, the system contains an imido-acid salt and an amine. In still other embodiments, the system contains an imido-acid salt, an amine, and one or more additional components, such as ionic liquids or imidazoles. Volatile compounds from a gas stream (e.g., a natural gas stream or a flue gas stream) can be reduced according to this method.

Further described herein is a method for sweetening a natural gas feed stream. The method includes contacting the natural gas feed stream with an effective amount of a system as described herein to form a purified natural gas feed stream and a gas-rich system.

Drug Delivery

The imido-acid salts including therapeutic agents as described herein can be used to deliver a therapeutically treat a subject. Generally, when such therapeutic agents are prepared as part of the imido-acid salts, as disclosed herein, the therapeutic agents can still maintain their efficacy, and can even have their efficacy enhanced by being part of the imido-acid salt. For example, when an imido-acid salt having a therapeutic agent as one or more of its cations or anions is administered to a subject, the therapeutic agent will dissociate from the ionic liquid and be available to the subject in the same way as had a solid form (e.g., tablet) or solution of the therapeutic agent been administered.

Depending on the particular ions, the disclosed imido-acid salt compositions can be used to treat a subject diagnosed with, for example, endocrine disorders, diabetes, infertility, hormone deficiencies, osteoporosis, ophthalmological disorders, neurodegenerative disorders, Alzheimer's disease, dementia, Parkinson's disease, multiple sclerosis, Huntington's disease, cardiovascular disorders, atherosclerosis, hyper-coagulable states, hypo-coagulable states, coronary disease, cerebrovascular events, metabolic disorders, obesity, vitamin deficiencies, renal disorders, renal failure, haematological disorders, anemia of different entities, immunologic and rheumatologic disorders, autoimmune diseases, immune deficiencies, infectious diseases, viral infections, bacterial infections, fungal infections, parasitic infections, neoplastic diseases, multi-factorial disorders, impotence, chronic pain, depression, and different fibrosis states.

Dosage forms for topical administration of the compounds described herein or derivatives thereof include ointments, powders, sprays, and inhalants. The compounds described herein or derivatives thereof are admixed under sterile conditions with a physiologically acceptable carrier and any preservatives, buffers, or propellants as can be required. Ophthalmic formulations, ointments, powders, and solutions are also contemplated as being within the scope of the compositions.

Administration of the compounds and compositions described herein or pharmaceutically acceptable salts thereof to a subject can be carried out using therapeutically effective amounts of the compounds and compositions described herein or pharmaceutically acceptable salts thereof as described herein for periods of time effective to treat a disorder.

The effective amount of the compounds and compositions described herein or pharmaceutically acceptable salts thereof as described herein can be determined by one of ordinary skill in the art and includes exemplary dosage amounts for a mammal of from about 0.5 to about 200 mg/kg of body weight of active compound per day, which can be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. The expression effective amount, when used to describe an amount of compound in a method, refers to the amount of a compound that achieves the desired pharmacological effect or other effect, for example an amount that results in bacterial enzyme inhibition.

Those of skill in the art will understand that the specific dose level and frequency of dosage for any particular subject can be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods and combinations of various features of the compounds and methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. A compound of the following formula:

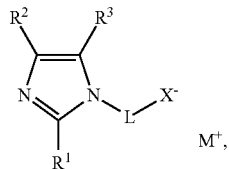

wherein:
L is substituted or unsubstituted $C_{1-20}$ alkyl;
$M^+$ is substituted or unsubstituted imidazolium;
$R^1$, $R^2$, and $R^3$ are each hydrogen; and
$X^-$ is a carboxylate.

2. The compound of claim 1, wherein L is substituted or unsubstituted $C_{1-6}$ alkyl.

3. A composition comprising the compound of claim 1 and a pharmaceutically acceptable carrier.

4. An ionic liquid, comprising:
a substituted or unsubstituted imidazolium cation; and
an anion, wherein the anion includes a compound of the following formula:

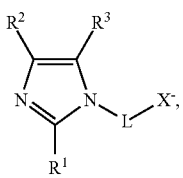

wherein:
L is substituted or unsubstituted $C_{1-20}$ alkyl;
$R^1$, $R^2$, and $R^3$ are each hydrogen; and
$X^-$ is carboxylate.

5. A method for reducing a volatile compound from a stream, comprising contacting the stream with a system comprising:
water; and
a compound of the following formula:

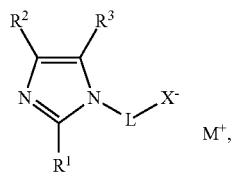

wherein:
L is substituted or unsubstituted $C_{1-20}$ alkyl;
$M^+$ is substituted or unsubstituted imidazolium;
$R^1$, $R^2$, and $R^3$ are each hydrogen; and
$X^-$ is carboxylate.

6. The method of claim 5, wherein the volatile compound is carbon dioxide, sulfur dioxide, or hydrogen sulfide.

7. The method of claim 5, wherein the system further comprises an ionic liquid.

8. The method of claim 5, wherein the stream is a gas stream or a liquid stream.

9. The method of claim 8, wherein the gas stream is a natural gas stream or a flue gas stream.

10. The method of claim 5, wherein the system further comprises a substituted or unsubstituted imidazole.

11. The method of claim 10, wherein the imidazole is an N-functionalized imidazole.

12. The method of claim 11, wherein the N-functionalized imidazole is an N-alkyl imidazole, an N-alkenyl imidazole, an N-alkynyl imidazole, or an N-aryl imidazole.

13. The method of claim 5, wherein the system further comprises an amine.

14. The method of claim 13, wherein the amine is a monoamine, a diamine, or a polyamine.

15. The method of claim 13, wherein the amine is selected from the group consisting of primary amines, secondary amines, tertiary amines, and cyclic amines.

16. The method of claim 13, wherein the amine has the following structure:

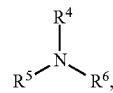

wherein
$R^4$, $R^5$, and $R^6$ are each independently selected from the group consisting of hydrogen, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{1-20}$ heteroalkyl, substituted or unsubstituted $C_{2-20}$ heteroalkenyl, substituted or unsubstituted $C_{2-20}$ heteroalkynyl, substituted or unsubstituted cycloalkyl, substituted or unsubstituted heterocycloalkyl, substituted or unsubstituted aryl, substituted or unsubstituted heteroaryl, substituted or unsubstituted amino, substituted or unsubstituted alkoxyl, substituted or unsubstituted aryloxyl, silyl, siloxyl, cyano, thio, and nitro.

17. The method of claim 16, wherein the primary amine is selected from the group consisting of monoethanolamine, diglycolamine, and 2-amino-2-methylpropanol.

18. The method of claim 16, wherein the secondary amine is selected from the group consisting of diethanolamine, and diisopropanolamine.

19. The method of claim 16, wherein the tertiary amine is N-methyldiethanolamine.

20. The method of claim 16, wherein the cyclic amine is substituted or unsubstituted piperazine.

21. A method for sweetening a natural gas feed stream, comprising:
(a) contacting the natural gas feed stream with a system comprising water and a compound of the following formula:

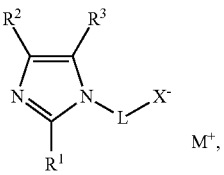

wherein:
L is substituted or unsubstituted $C_{1-20}$ alkyl;
$M^+$ is substituted or unsubstituted imidazolium;
$R^1$, $R^2$, and $R^3$ are each hydrogen; and
$X^-$ is carboxylate, to form a purified natural gas feed stream and a gas-rich system; and
(b) separating the purified natural gas feed stream from the gas-rich system.

22. The method of claim 21, wherein the system further comprises an amine, a substituted or unsubstituted imidazole, an ionic liquid, or a mixture of these.

23. A system, comprising:
water; and
a compound of the following formula:

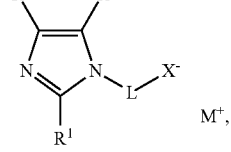

wherein:
L is substituted or unsubstituted $C_{1-20}$ alkyl;
$M^+$ is substituted or unsubstituted imidazolium;
$R^1$, $R^2$, and $R^3$ are each hydrogen; and
$X^-$ is carboxylate.

24. The system of claim 23, further comprising an amine, a substituted or unsubstituted imidazole, an ionic liquid, or a mixture of these.

* * * * *